(12) United States Patent
Hotter et al.

(10) Patent No.: US 9,510,931 B2
(45) Date of Patent: Dec. 6, 2016

(54) REINFORCED TISSUE PATCH

(71) Applicant: Covidien LP, Mansfield, MA (US)

(72) Inventors: Joseph Hotter, Middletown, CT (US); Nilay Mukherjee, Acton, MA (US)

(73) Assignee: Covidien LP, Mansfield, MA (US)

( * ) Notice: Subject to any disclaimer, the term of this patent is extended or adjusted under 35 U.S.C. 154(b) by 70 days.

(21) Appl. No.: 14/245,064

(22) Filed: Apr. 4, 2014

(65) Prior Publication Data

US 2014/0222164 A1 Aug. 7, 2014

Related U.S. Application Data

(62) Division of application No. 12/914,436, filed on Oct. 28, 2010, now Pat. No. 8,690,960.

(60) Provisional application No. 61/263,967, filed on Nov. 24, 2009.

(51) Int. Cl.
*A61F 2/02* (2006.01)
*A61B 17/06* (2006.01)
*A61F 2/00* (2006.01)
*A61F 2/30* (2006.01)

(52) U.S. Cl.
CPC ........... *A61F 2/02* (2013.01); *A61B 17/06166* (2013.01); *A61F 2/0063* (2013.01); *A61B 2017/06176* (2013.01); *A61F 2/0045* (2013.01); *A61F 2002/30062* (2013.01); *A61F 2210/0004* (2013.01)

(58) Field of Classification Search
CPC ............... A61B 17/06166; A61B 2017/06176; A61F 2/02; A61F 2/0063; A61F 2/0045; A61F 2002/30062; A61F 2210/0004
USPC ............... 606/151, 152, 153, 154, 155, 213, 214,606/216, 228–231
See application file for complete search history.

(56) References Cited

U.S. PATENT DOCUMENTS

| | | | | |
|---|---|---|---|---|
| 3,522,637 | A | * | 8/1970 | Brumlik ..................... 24/445 |
| 3,646,615 | A | | 3/1972 | Ness |
| 3,708,833 | A | * | 1/1973 | Ribich et al. ................ 24/450 |
| 4,769,038 | A | * | 9/1988 | Bendavid et al. ........ 623/13.11 |
| 4,979,956 | A | | 12/1990 | Silvestrini |
| 5,195,542 | A | * | 3/1993 | Gazielly et al. ............. 128/898 |
| 5,425,747 | A | | 6/1995 | Brotz |
| 5,441,508 | A | * | 8/1995 | Gazielly et al. ............. 606/151 |
| 5,584,859 | A | | 12/1996 | Brotz |
| 5,593,441 | A | | 1/1997 | Lichtenstein et al. |
| 5,743,917 | A | | 4/1998 | Saxon |
| 5,797,960 | A | * | 8/1998 | Stevens et al. ............. 606/213 |
| 5,855,619 | A | | 1/1999 | Caplan et al. |
| 5,931,855 | A | | 8/1999 | Buncke |
| 6,270,517 | B1 | * | 8/2001 | Brotz ......................... 606/228 |
| 6,368,356 | B1 | | 4/2002 | Zhong et al. |
| 6,383,201 | B1 | | 5/2002 | Dong |
| 6,599,310 | B2 | * | 7/2003 | Leung et al. ............... 606/228 |

(Continued)

OTHER PUBLICATIONS

European Search Report EP10177651.6-1526 dated Dec. 14, 2010.

*Primary Examiner* — Gregory Anderson
*Assistant Examiner* — Son Dang

(57) ABSTRACT

A method of improving the mechanical properties of a tissue patch is provided. The method includes the steps of providing a tissue patch and placing at least one barbed suture along at least a portion of the tissue patch. The method may further include the step of placing one or more additional barbed sutures in a laterally spaced relation to the barbed suture. The barbed suture may be biodegradable or non-biodegradable.

8 Claims, 7 Drawing Sheets

(56) References Cited

U.S. PATENT DOCUMENTS

| | | | |
|---|---|---|---|
| 6,599,323 B2 | 7/2003 | Melican et al. | |
| 6,638,312 B2 | 10/2003 | Plouhar et al. | |
| 6,669,706 B2 | 12/2003 | Schmitt et al. | |
| 6,692,499 B2 | 2/2004 | Tormala et al. | |
| 6,736,854 B2 | 5/2004 | Vadurro et al. | |
| 6,746,458 B1 * | 6/2004 | Cloud | 606/151 |
| 6,852,330 B2 | 2/2005 | Bowman et al. | |
| 6,893,452 B2 | 5/2005 | Jacobs | |
| 6,921,412 B1 * | 7/2005 | Black et al. | 606/213 |
| 6,939,364 B1 * | 9/2005 | Soltz et al. | 606/214 |
| 6,946,003 B1 | 9/2005 | Wolowacz et al. | |
| 7,011,688 B2 | 3/2006 | Gryska et al. | |
| 7,156,862 B2 | 1/2007 | Jacobs et al. | |
| 7,160,333 B2 | 1/2007 | Plouhar et al. | |
| 7,303,577 B1 * | 12/2007 | Dean | 606/215 |
| 7,351,250 B2 * | 4/2008 | Zamierowski | 606/215 |
| 7,368,124 B2 | 5/2008 | Chun et al. | |
| 7,371,253 B2 | 5/2008 | Leung et al. | |
| 7,404,819 B1 | 7/2008 | Darios et al. | |
| 2002/0120348 A1 | 8/2002 | Melican et al. | |
| 2003/0216758 A1 * | 11/2003 | Signore | 606/151 |
| 2004/0010275 A1 | 1/2004 | Jacobs et al. | |
| 2004/0039415 A1 * | 2/2004 | Zamierowski | 606/215 |
| 2004/0060409 A1 | 4/2004 | Leung et al. | |
| 2005/0080454 A1 * | 4/2005 | Drews et al. | 606/221 |
| 2005/0113938 A1 | 5/2005 | Jamiolkowski et al. | |
| 2005/0149119 A1 * | 7/2005 | Koyfman et al. | 606/228 |
| 2005/0182445 A1 * | 8/2005 | Zamierowski | 606/213 |
| 2007/0129811 A1 | 6/2007 | Plouhar et al. | |
| 2008/0027470 A1 * | 1/2008 | Hart et al. | 606/151 |
| 2008/0077181 A1 | 3/2008 | Jones et al. | |
| 2008/0188936 A1 * | 8/2008 | Ball et al. | 623/13.14 |
| 2009/0018655 A1 | 1/2009 | Brunelle et al. | |
| 2009/0024226 A1 | 1/2009 | Lesh | |
| 2009/0030526 A1 | 1/2009 | Sommerich et al. | |
| 2009/0112236 A1 * | 4/2009 | Stopek | 606/151 |
| 2009/0210006 A1 * | 8/2009 | Cohen et al. | 606/232 |
| 2009/0228021 A1 * | 9/2009 | Leung | 606/139 |
| 2010/0094079 A1 * | 4/2010 | Inman et al. | 600/30 |
| 2010/0211174 A1 * | 8/2010 | Scarborough | 623/13.14 |
| 2012/0077661 A1 | 3/2012 | Oonishi et al. | |

\* cited by examiner

REINFORCED TISSUE PATCH

CROSS-REFERENCE TO RELATED APPLICATIONS

This application is a divisional of U.S. patent application Ser. No. 12/914,436 filed Oct. 28, 2010, now U.S. Pat. No. 8,690,960, which claims benefit of U.S. Provisional Application No. 61/263,967 filed Nov. 24, 2009, and the disclosures of each of the above-identified applications are hereby incorporated by reference in their entirety.

BACKGROUND

1. Technical Field

The present disclosure relates to patches for use in tissue repair. More particularly, the present disclosure relates to tissue patches having improved mechanical properties.

2. Background of Related Art

Autograft, allograft and xenograft tissue patches are currently used for a variety of reinforcement applications, such as hernia, anterior cruciate ligament and rotator cuff repairs. Advanced tissue processing methods have been developed that minimize the potential for an exaggerated and undesirable immunological response, for allografts and xenograft tissue types, in particular. Unfortunately, in these reinforcement applications, undesirable immunological responses are not the only issue affecting the tissue patches.

The mechanical properties (tensile strength, initial tensile modulus, suture pullout strength, etc.) of these traditional tissue patches are less than optimal. Because tissue patches are generally used to replace tissue in areas subject to wear, these areas tend to experience significant loads that greatly affect the tissue patch. One such area of high wear is in the rotator cuff where implanted tissue must provide significant load bearing support, specifically when used as an intercalary patch.

In a rotator cuff repair, a reinforced tissue patch may facilitate the repair construct by one or more of the following mechanisms: i) by providing a 'bridge' to an intercalary structure between the rotator cuff tendon and the humerus in instances where shortening of the rotator cuff tendon results in a gap; ii) by augmenting the repair construct by adding additional support when the rotator cuff tendon is insufficient to handle the loads the repair construct creates; iii) by acting as a matrix for tissue repair to enhance the biological repair and reformation of the rotator cuff biomechanical integrity; and iv) by aiding recreation of the normal rotator cuff cable-like mechanism required for normal range of motion and strength.

Improving the mechanical properties of a tissue patch may extend the life of the patch, may reduce the thickness of the patch necessary to complete a given procedure, may allow for different types of tissue to be used, may expand the range of applications, and/or may facilitate attachment with adjacent tissue, amongst other benefits.

Therefore, it would be beneficial to have a reinforced tissue patch and means of improving the mechanical properties of tissue patches.

SUMMARY

Accordingly, a method of improving the mechanical properties of a tissue patch is provided. The method includes the steps of providing a tissue patch and placing at least one barbed suture along at least a portion of the tissue patch. The method may further include the step of placing one or more additional barbed sutures in a laterally spaced relation to the at least one barbed suture. The at least one barbed suture may be biodegradable.

The method of improving the mechanical properties of a tissue patch may further include the step of securing the tissue patch to a patient using the at least one barbed suture placed therethrough. The method may include placing at least one additional barbed suture at an angle relative to the previously placed at least one barbed suture. The tissue patch may comprise allograft, xenograft or autologous tissue.

Also provided is a method of repairing a rotator cuff using a reinforced tissue patch. The method includes the steps of accessing a surgical site including a humerus and a rotator cuff tendon, creating a defect in the humerus, providing a reinforced tissue patch having a first end and a second end, attaching the first end of the patch within the defect of the humerus such that the patch extends from the humerus and attaching the second end of the reinforced tissue patch to the rotator cuff tendon. The method may further include debriding the rotator cuff tendon.

In the method of repairing a rotator cuff, the step of providing a reinforced tissue patch may include attaching a bone segment to the first end of the patch. The step of accessing the humerus and the rotator cuff may include accessing the humerus and the rotator cuff via an access port. The rotator cuff tendon may be selected from the group consisting of a supraspinatus tendon, an infraspinatus tendon, a teres minor tendon, a subscapularis tendon, and a long head tendon. The bone segment of the patch may be a bone plug. The step of attaching the patch to the rotator cuff tendon may be performed by an attaching technique selected from the group consisting of anchoring, suturing, adhering, stapling, screwing, plugging, and press-fitting.

The disclosed method of rotator cuff repair, may further include the step of applying energy to the surgical site selected from the group consisting of ultrasonic energy, pulsed electromagnetic field energy, current energy, and pressure hyperbaric energy. The reinforced tissue patch may comprise a material selected from the group consisting of autogenous, allogenic, xenogenic and synthetic. The patch and the bone segment used in the rotator cuff repair may be coupled to each other by using mechanical means selected from the group consisting of interference fitting, pinning, stapling, adhering and combinations thereof.

Also provided is a reinforced tissue including a tissue patch and at least one barbed suture received within the tissue patch. The at least one barbed suture may extend along a length of the tissue patch. The at least one barbed suture may form at least one of a Z-pattern and an X-pattern. The at least one barbed suture may be in a spiral configuration. The tissue patch may comprise allograft, xenograft or autologous tissue.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
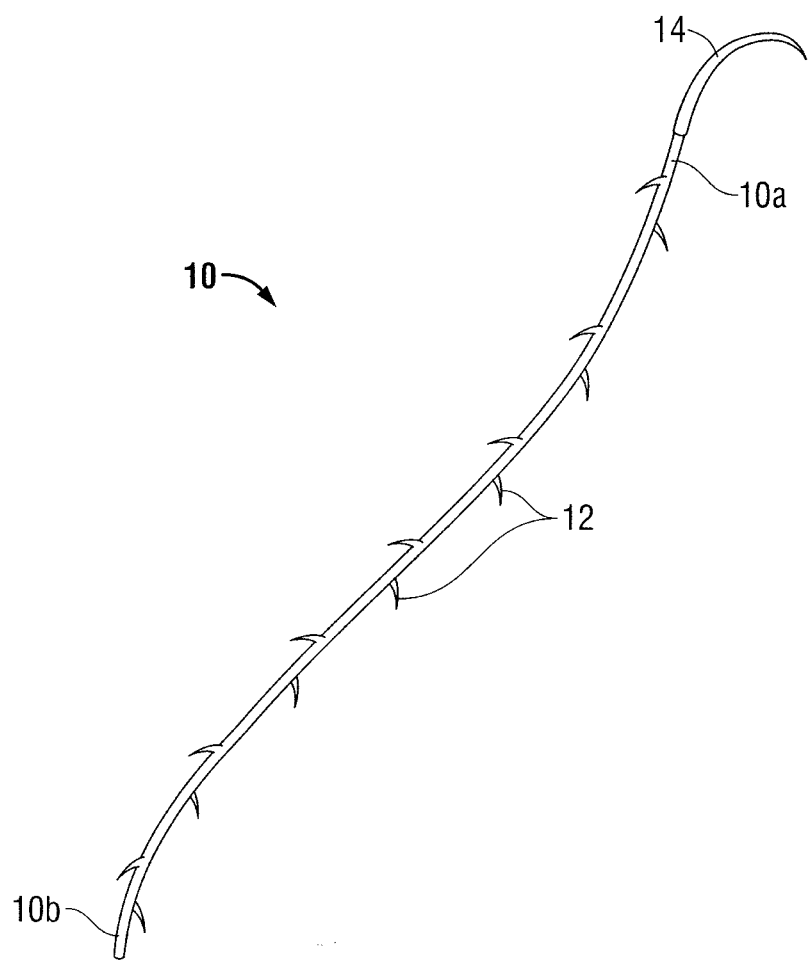
FIG. 1 is a perspective view of a barbed suture according to an embodiment of the present disclosure.

As shown in FIG. 1, an embodiment of a barbed suture capable of use with the aspects of the present disclosure is shown generally as suture 10. Although shown as a monofilament thread, it is envisioned that suture 10 may be formed from braided threads, multifilament threads and other surgical fibers.

Although shown having a circular cross-sectional geometry, the cross-sectional geometry of suture 10 may be of any suitable shape. Suture 10 may be formed of degradable materials, non-degradable materials, and combinations thereof. More particularly, suture 10 may be formed of a degradable material selected from the group consisting of polyesters, polyorthoesters, polymer drugs, polydroxybutyrates, lactones, proteins, cat gut, collagens, carbonates, homopolymers thereof, copolymers thereof, and combinations thereof. In other embodiments, suitable degradable materials which may be utilized to form suture 10 include natural collagenous materials or synthetic resins including those derived from alkylene carbonates such as trimethylene carbonate, tetramethylene carbonate, and the like; caprolactone; dioxanone; glycolic acid; lactic acid; homopolymers thereof; copolymers thereof; and combinations thereof. In some embodiments, glycolide and lactide based polyesters, especially copolymers of glycolide and lactide, may be utilized to form suture 10.

Suitable non-degradable materials which may be utilized to form suture 10 include polyolefins, such as polyethylene (including ultra high molecular weight polyethylene) and polypropylene; copolymers of polyethylene and polypropylene, and blends of polyethylene and polypropylene; polyamides (such as nylon); polyamines; polyimines; polyesters such as polyethylene terephthalate; polytetrafluoroethylene; polyether-esters such as polybutester; polytetramethylene ether glycol; 1,4-butanediol; polyurethanes; and combinations thereof. Other suitable non-degradable materials include silk, cotton, linen, carbon fibers, and the like. The polypropylene may be isotactic polypropylene or a mixture of isotactic and syndiotactic or atactic polypropylene.

Suture 10 may be formed using any technique within the purview of those skilled in the art, such as, for example, extrusion, molding and/or spinning. In some embodiments, suture 10 may include a yarn made of more than one filament, which may contain multiple filaments of the same or different materials. Where suture 10 is made of multiple filaments, suture 10 may be made using any known technique such as, for example, braiding, weaving or knitting. Suture 10 may also be combined to produce a non-woven suture. Suture 10 may be drawn, oriented, crinkled, twisted, commingled or air entangled to form yarns as part of the suture forming process. In one embodiment, a multifilament suture may be produced by braiding. The braiding may be done by any method within the purview of those skilled in the art.

With reference still to FIG. 1, suture 10 includes a plurality of barbs 12 formed along a length thereof. Barbs 12 are radially and longitudinally spaced along suture 10 and may be formed using any suitable method. As will be discussed in further detail below, barbs 12 on suture 10 may extend in the same direction along the entire length thereof, or may instead extend in one direction on a first portion of suture 10 and may extend in an opposite direction on a second portion of suture 10. Barbs 12 may be of uniform size and shape along the length of suture 10. Alternatively, barbs 12 may be of different sizes and shapes. Either or both ends 10a, 10b of suture 10 may include a sharpened tip or a curved or straight needle 14 configured for penetrating tissue.

Barbs 12 may be arranged in any suitable pattern, for example, helical, linear, or randomly spaced. The pattern may be symmetrical or asymmetrical. The number, configuration, spacing and surface area of barbs 12 may vary depending upon the tissue in which suture 10 is used, as well as the composition and geometry of the suture material. Additionally, the proportions of barbs 12 may remain relatively constant while the overall length of barbs 12 and the spacing of barbs 12 may be determined by the type of tissue being reinforced and/or the type of tissue to which the reinforced tissue is being attached. For example, if suture 10 is to be used to reinforce a tissue patch for a tendon, barbs 12 may be made relatively short and more rigid to facilitate entry into this rather firm tissue. Alternatively, if suture 10 is intended to be used to reinforce softer tissue, barbs 12 may be made longer and spaced further apart to increase the ability of suture 10 to grip the soft tissue.

The surface area of barbs 12 may also vary. For example, fuller-tipped barbs may be made of varying sizes designed for specific surgical applications. For reinforcing and/or joining relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum reinforcing and/or anchoring properties. In particular embodiments, a single directional suture may have both large and small barbs; in other embodiments a bi-directional suture may have both large and small barbs. Barbs 12 may include geometrical shapes such as round, triangular, square, oblique, elliptical, octagonal, rectangular, and flat.

When fabricated from a degradable material, suture 10 maintains its structural integrity after implantation for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

The formation of barbs 12 on suture 10 may be utilized to change the degradation time of suture 10 as described in U.S. Patent Application Publication No. 2008/0109036, filed on Nov. 2, 2006, entitled "Long Term Bioabsorbable Barbed Sutures", the entire contents of which are incorporated by reference herein.

Figure 2:
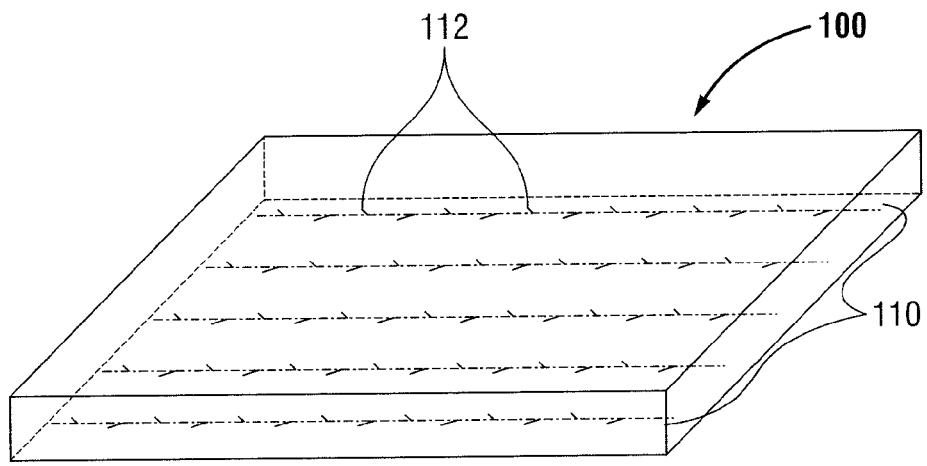
FIG. 2 is a perspective view of a reinforced tissue patch according to an embodiment of the present disclosure.
Figure 3:
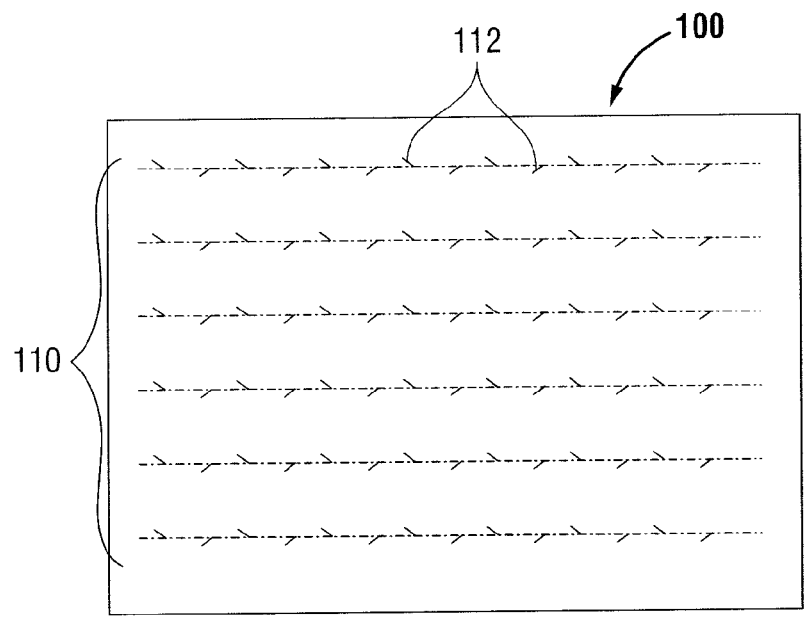
FIG. 3 is a top view of the reinforced tissue patch of FIG. 2.

Referring now to FIGS. 2 and 3, a first embodiment of a tissue patch according to an aspect of the present disclosure is shown generally as tissue patch 100. Tissue patch 100 includes a plurality of sutures 110 received therein. Sutures 110 extend along a length of tissue patch 100 and are laterally spaced from one another. Each of sutures 110 includes a plurality of barbs 112 formed along a length thereof. Sutures 110 are arranged such that barbs 112 extend in the same direction. Suture 110 may be coated and/or impregnated with various substances, as will be discussed in detail below. Although shown as a series of protrusions extending from suture 110, as used herein, "barbs" refer to any features that permit reception of a suture through tissue in a first direction and prevent withdrawal of the suture in a second direction.

Still referring to FIGS. 2 and 3, reinforced tissue patch 100 may include an autograft, allograft or xenograft. Tissue patch 100 may include any type of tissue, such as connective tissue and soft tissue. Tissue patch 100 may include any shape and may be configured for use in countless procedures. Although shown completely maintained within tissue patch 100, it is appreciated that sutures 110 may include a needle (not shown) or a sharpened tip (not shown) for facilitating insertion of sutures 110 into and through tissue patch 100. Sutures 110 may be placed through tissue patch 100 prior to harvesting tissue patch 100 from a patient donor or other source of tissue. Sutures 110 may instead be placed through tissue patch 100 during harvesting of tissue patch 100 or post harvesting of tissue patch 100. Additionally, sutures 110 may be placed through tissue patch 100 prior to implantation, during implantation, or upon implantation of tissue patch 100 within a body. Sutures 110 are configured and placed to improve the mechanical performance (tensile strength, initial tensile modulus, suture pullout strength, etc.) of tissue patch 100.

Depending on the type of tissue from which tissue patch 100 is formed, tissue patch 100 may include clearly defined grains or striations (not shown). Sutures 110 may be placed parallel to and/or at an angle with respect to the grains to further change the mechanical properties of tissue patch 100. For example, suture 110 may be placed across the grains of tissue patch 100 to prevent stretching of tissue patch 100 along the grains. Alternatively, suture 110 may be placed parallel to the grains to permit stretching of tissue patch 100. Tissue patch 100 may also include multiple layers (not shown). To improve the mechanical properties of tissue patch 100 having multiple layers, sutures 110 are woven back and forth between the tissue layers. In this manner, a first layer (not shown) of tissue patch 100 would be secured to a second layer (not shown) of tissue patch 100. Multiple layers of tissue patch 100 may be secured and reinforced in this manner.

As discussed above, barbs 112 of suture 110 may be modified to affect the properties of sutures 110. The modifications to suture 110 and barbs 112 may further change the mechanical properties of reinforced tissue patch 100.

Figure 4:
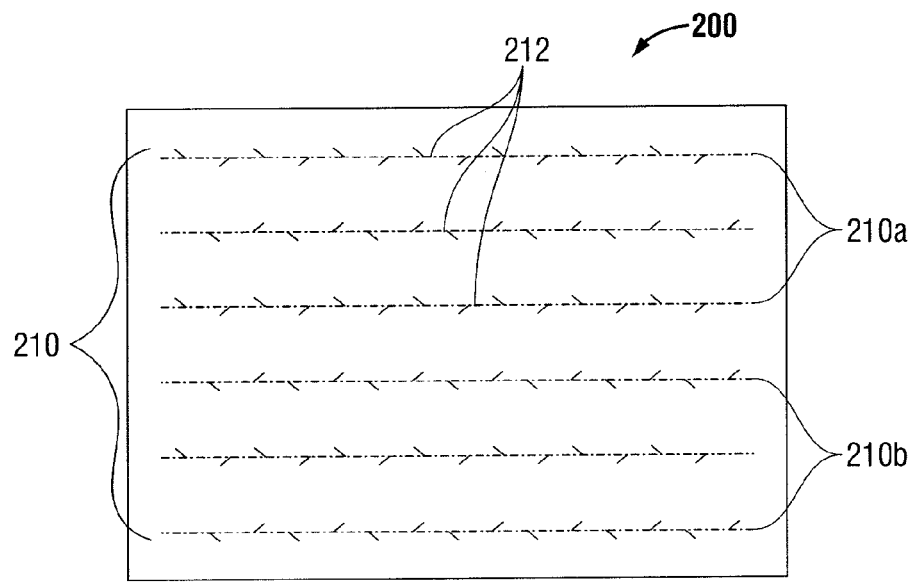
FIG. 4 is a top view of a reinforced tissue patch according to another embodiment of the present disclosure.

Turning to FIG. 4, reinforced tissue patch 200 includes a plurality of sutures 210 extending the length thereof. Each of sutures 210 include barbs 212. Sutures 210 are placed in tissue patch 200 such that barbs 212 of every other suture 210a extend in a first direction and barbs 212 of the remaining sutures 210b extend in an opposite direction. In this manner, sutures 210a prevent tissue patch 200 from being stretched in a first longitudinal direction and sutures 210b prevent tissue patch 200 from being stretched in a second longitudinal direction.

Figure 5:
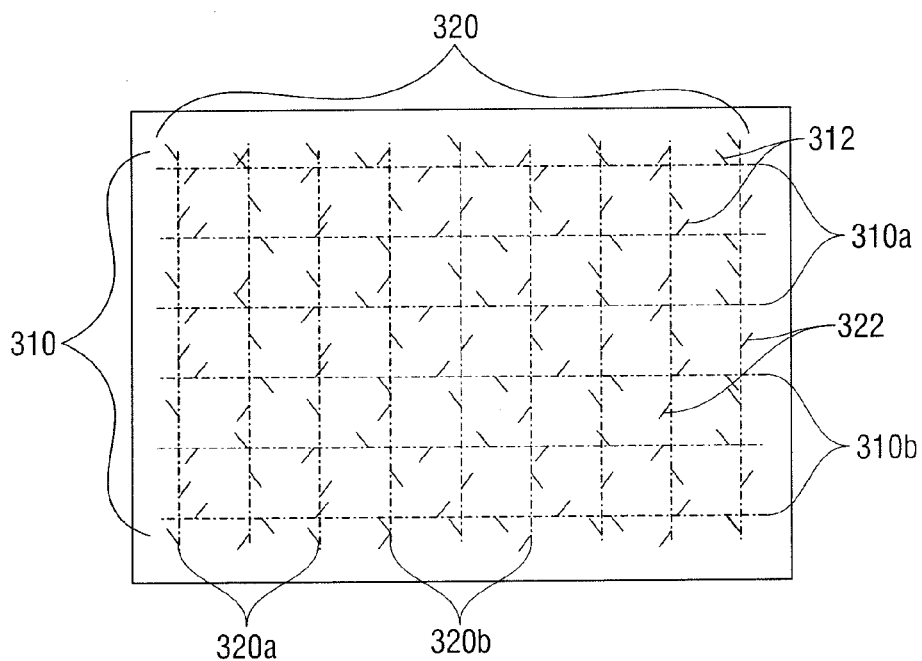
FIG. 5 is a top view of a reinforced tissue patch according to yet another embodiment of the present disclosure.

With reference now to FIG. 5, reinforced tissue patch 300 includes a first plurality of sutures 310 extending a length thereof and a second plurality of sutures 320 extending a width thereof. Each of sutures 310, 320 include barbs 312, 322, respectively. Sutures 310 are placed in tissue patch 300 such that barbs 312 of every other suture 310a extend in a first longitudinal direction and barbs 312 of remaining sutures 310b extend in an opposite second longitudinal direction. Sutures 320 are placed in tissue patch 300 such that barbs 322 of every other suture 320a extend in a first lateral direction and barbs 322 of the remaining sutures 320b extend in an opposite second lateral direction. In this manner, sutures 310a, 310b prevent tissue patch 300 from being stretched in either longitudinal direction and sutures 320a, 320b prevent tissue patch 300 from being stretched in either lateral direction. Although not shown, it is envisioned that sutures 310, 320 may engage one another at the overlapping portions thereof. Either or both of sutures 310, 320 may be wrapped about other and/or respective barbs 312, 322 of sutures 310, 320 may be positioned to engage one another at the overlapping portions of sutures 310, 320.

Figure 6:
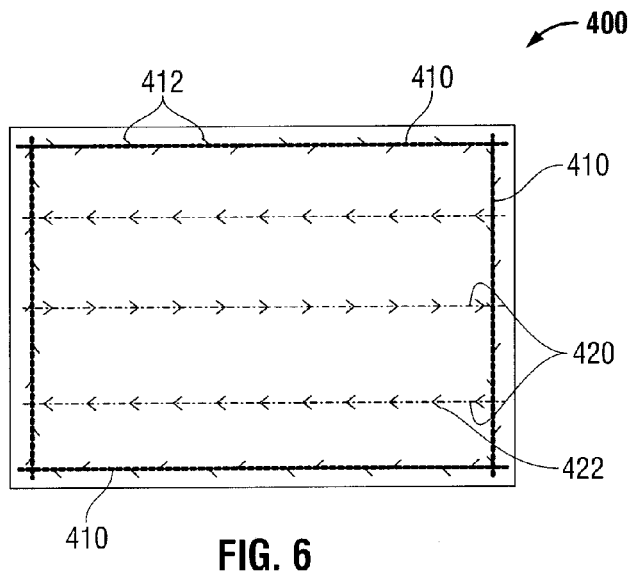
FIG. 6 is a top view of a reinforced tissue patch according to still another embodiment of the present disclosure.

Turning now to FIG. 6, tissue patch 400 includes sutures 410 extending about a perimeter of suture patch 400 and sutures 420 extending longitudinally through tissue patch 400. As shown, sutures 410 included barbs 412 formed in an alternating pattern along the length thereof. Suture 410 include a thicker diameter than sutures 420. The increased thickness of sutures 410 may make sutures 410 better suited for reinforcing the perimeter of tissue patch 400.

Figure 7:
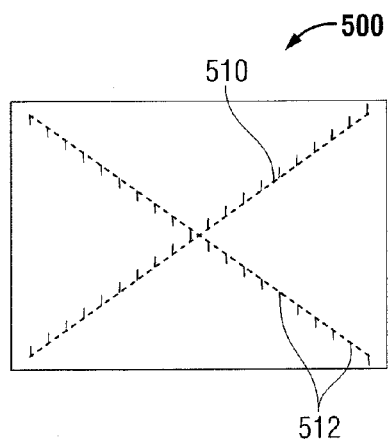
FIG. 7 is a top view of a reinforced tissue patch according to still yet another embodiment of the present disclosure.
Figure 8:
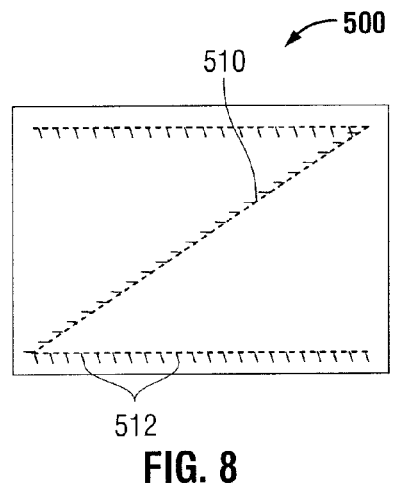
FIG. 8 is a top view of a reinforced tissue patch according to still yet another embodiment of the present disclosure.

With reference to FIGS. 7 and 8, as shown, sutures 510 are placed in a reinforced tissue patch 500 in an X-shaped pattern (FIG. 7), in a Z-shaped pattern (FIG. 8) or in any suitable arrangement to reinforce tissue patch 500. Barbs 512 are formed on a first surface of sutures 510.

Figure 9:
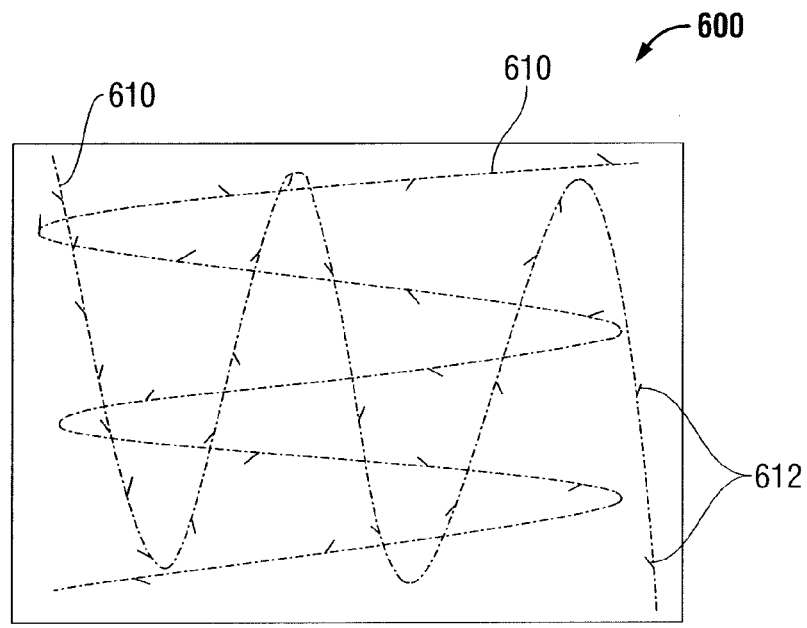
FIG. 9 is a top view of a reinforced tissue patch according to still yet another embodiment of the present disclosure.

Referring to FIG. 9, sutures 610 are placed through reinforced tissue patch 600 in an overlapping manner. In this manner, barbs 612 formed on one of sutures 610 may engage barbs 612 formed on the other of sutures 610 to further improve the mechanical properties of tissue patch 600.

Figure 10:
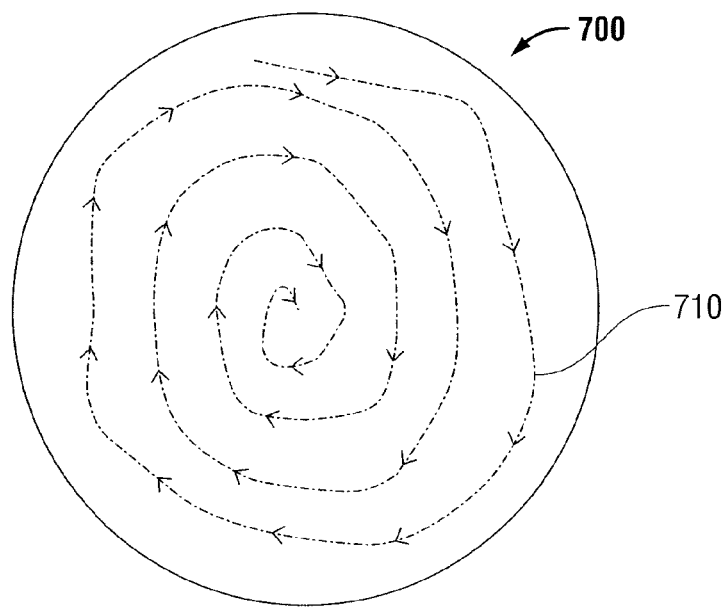
FIG. 10 is a top view of a reinforced tissue patch according to still yet another embodiment of the present disclosure.

Turning to FIG. 10, sutures 710 are placed through reinforced tissue patch 710 in a spiral configuration. As shown, tissue patch 710 includes a circular configuration, however, as discussed above, tissue patch 710 may include any configuration. It is envisioned that sutures 710 may be placed through tissue patch 700 in multiple spiral configurations and/or in overlapping spiral configurations at areas of increased stress and/or high wear to improve the mechanical properties of tissue patch 700.

Figure 11:
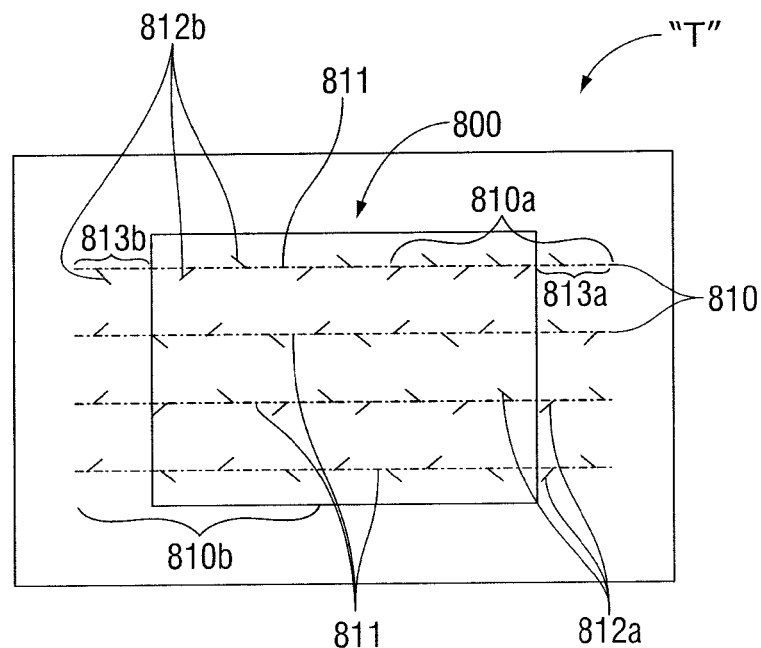
FIG. 11 is a top view of a reinforced tissue patch according to still yet another embodiment of the present disclosure.

With reference now to FIG. 11, reinforced tissue patch 800 is shown secured to tissue "T" of a patient. Tissue patch 800 includes sutures 810 extending therethrough. Sutures 810 include a first set of barbs 812a formed along a first portion 810a of suture 810 and a second set of barbs 812b formed along a second portion 810b of suture 810. First and second set of barbs 812a, 812b extend towards a center portion 811 of suture 810. Sutures 810 include excess portions 813a, 813b extending beyond tissue patch 800 that are used to secure tissue patch 800 to tissue "T". In this manner, in addition to providing reinforcement to tissue patch 800, sutures 810 are configured to secure tissue patch 800 to tissue "T" of a patient.

Figure 12:
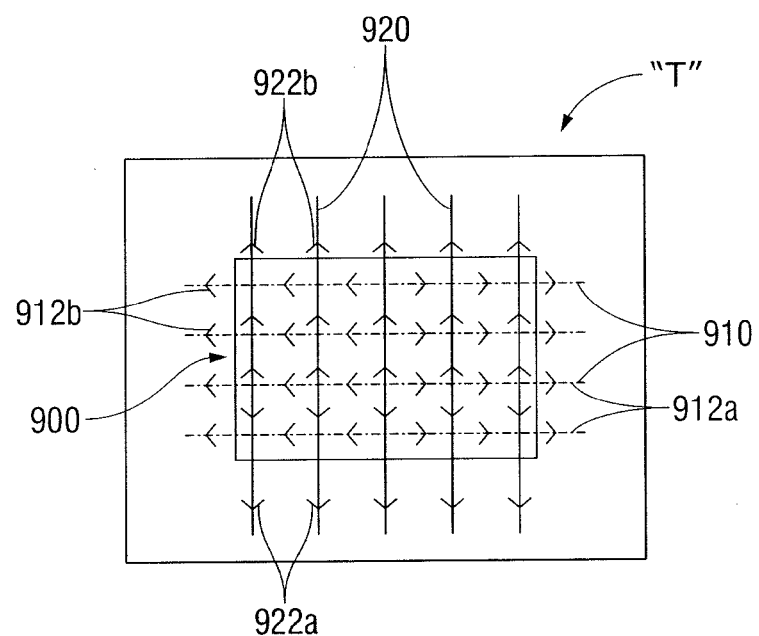
FIG. 12 is a top view of a reinforced tissue patch according to still yet another embodiment of the present disclosure.

Turning to FIG. 12, reinforced tissue patch 900 is substantially similar to tissue patch 800 described above, including sutures 910 extending longitudinally therethrough. Tissue patch 900 further includes suture 920 extending laterally therethrough. Sutures 910 are generally horizontal and include first and second sets of barbs 912a, 912b while sutures 920 are generally vertical and include first and second sets of barbs 920a, 920b. Sutures 910, 920 are generally perpendicular to each other and are configured to reinforce tissue patch 900 and to secure tissue patch 900 to tissue "T" of a patient.

The tissue patches and barbed sutures of the present disclosure may be coated or impregnated with one or more bioactive agents or useful substances which accelerate or beneficially modify the healing process. In certain embodiments, a coating may be formed from degradable polymers selected from the group consisting of lactones, carbonates, polyorthoesters, hydroxyalkoanates, hydroxybutyrates, bioactive agents, polyanhydrides, silicone, calcium stearoyl lactylates, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, any one of above disclosed sutures may be provided with a bioactive agent that will be deposited at the sutured site. The bioactive agent may be chosen for its antimicrobial properties, capability for promoting wound repair and/or tissue growth, or for specific indications such as thrombosis. In some embodiments, combinations of such agents may be applied to the suture before, during, or after formation of barbs 12.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In other embodiments, suitable antimicrobial agents may be soluble in one or more solvents.

In some embodiments, the following bioactive agents may be used alone or in combination with other bioactive agents described herein: an anthracycline, doxorubicin, mitoxantrone, a fluoropyrimidine, a folic acid antagonist, methotrexate, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, erythromycin, azithromycin, clindamycin, syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Other suitable bioactive agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly (ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, α,α-dipyridyl, β-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum ; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized on or with the tissue patches and/or barbed sutures of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof. Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Bioactive agents may be applied onto the above disclosed tissue patches and/or barbed sutures utilizing any method within the purview of one skilled in the art including, for example, dipping, spraying, vapor deposition, brushing, solvent evaporation, compounding and the like. In embodiments, a bioactive agent may be deposited within the barb angles, that is, the angle formed between the barbs on the suture and elongated body of the suture. This placement of the bioactive agent beneath barbs on the suture places the bioactive agent at precisely defined locations within a tissue patch, which thereby provides a unique controlled and sustained release dosage form. In other embodiments, the tissue patch may be dipped into a solution containing a bioactive agent in the operating room, prior to implantation.

Any of the above disclosed sutures may also include, for example, biologically acceptable plasticizers, antioxidants and colorants, which may be impregnated into the filament(s) utilized to form the suture or included in a coating thereon.

Figure 13:
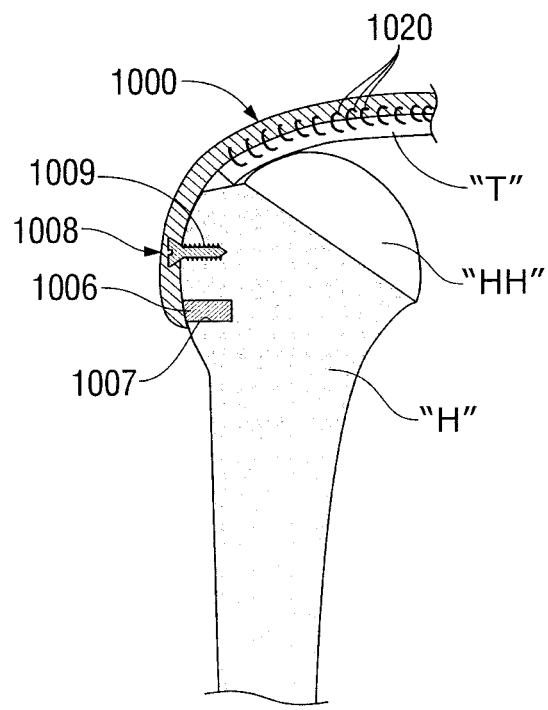
FIG. 13 is a partial cross-sectional side view of a rotator cuff repair using a reinforced tissue patch according to an embodiment of the present disclosure.
Figure 14:
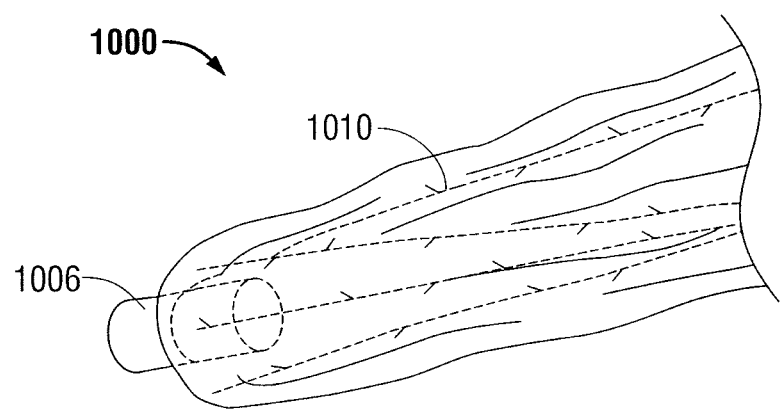
FIG. 14 is a bottom view of an end of the reinforced tissue patch of FIG. 13, including a bone plug attached thereto.

With reference now to FIG. 13, a method of repairing a rotator cuff in a patient using a reinforced tissue patch according to an embodiment of the present disclosure will now be described. Because the composition of the tissue patch, as well as, the configuration and placement of the barbed sutures reinforcing the tissue patch may be determined by the surgeon on a procedure by procedure basis, the reinforced tissue patch used to describe the rotator cuff repair method will be referred to generally as reinforced tissue patch 1000. It is appreciated that various configurations of reinforced tissue patches may be utilized in repair discussed below, including the reinforced tissue patches disclosed above. It should be noted that the methods described in the present disclosure may apply to the repair of other tendons in the human body. It should also be noted that this method of the present disclosure may be applied to repair bone-tendon mechanisms of animals other than humans.

Still referring to FIG. 13, the method of repairing a rotator cuff includes accessing a surgical site, including a humerus "H" and a rotator cuff tendon "T". Rotator cuff tendon "T" may be for example, a supraspinatus tendon, an infraspinatus tendon, a teres minor tendon, a subscapularis tendon, and/or a long head tendon. Other potential tendons in various anatomical locations are also contemplated. The surgical site is accessed by performing traditional open surgery, arthroscopic surgery, and/or a mini-open surgery.

Prior to accessing the surgical site, tissue patch 1000 is either harvested from the patient (autograft), from a donor patient (allograft), from a donor animal (xenograft), is grown or produced. Regardless of the source, reinforced tissue patch 1000 is modified in the manner discussed above, to reinforce tissue patch 1000. As discussed above, this may occur prior to, during or after harvesting of the tissue. Modifying tissue patch 1000 includes placing barbed sutures 1010 longitudinally, laterally, overlapping, criss-crossing, or in any other suitable configuration through tissue patch 1000 to reinforce tissue patch 1000.

With reference still to FIG. 13, after the surgical site has been accessed, rotator cuff tendon "T" is then debrided, in order to remove frayed intra-substance tissue from the torn tendon. Afterwards, rotator cuff tendon "T" is pulled back into anatomical position and secured to reinforced tissue patch 1000 by using attaching means, for example, but not limited to, sutures, suture anchors, etc. In some instances the tendon may have shortened due to degeneration and contracture and may not be able to be reapposed to the anatomical insertion point without creating undue tension. In these instances, reinforced tissue patch 1000 acts as an intercalary 'bridge' to span the gap. In other instances, an open 'window' remains after the repair and it is desirable to close the hole which may be responsible for residual pain in some patients.

The method of the present disclosure provides the capability of achieving both of these objectives, since the strong biomechanical properties of the disclosed embodiments protect the extensor mechanisms and facilitate natural healing. After a damaged rotator cuff tendon "T" (e.g., a supraspinatus tendon) has been debrided, a foot-print in the top portion of humerus "H" is prepared by performing a light decortication. This foot-print enhances biological incorporation and reattachment of rotator cuff tendon "T" and/or reinforced tissue patch 1000 to humerus "H", thus recreating a natural-like insertion site. In the event reinforced tissue patch 1000 includes one or more bone segments 1005 attached thereto which may be formed into one or more bone plugs 1006, a defect 1008 is also created in humerus "H" with a configuration appropriate to correspond to the shape of bone plug 1006.

Once the foot-print is prepared, a drilling instrument, or any other defect creating device, may be used to create defect (e.g., hole or cavity) 1007 in humerus "H". In some embodiments, the diameter of defect 1007 is dimensioned to be equal or slightly smaller than a diameter of bone plug 1006 such that a compression and/or interference fit is created when bone plug 1006 is firmly positioned within defect 1007. Additionally, or in the event reinforce tissue patch 1000 does not include one or more bone segments, a securement means 1008 may be utilized including mechanical means such as interference screws 1009, suture anchor etc, or other means such as adhesives, etc, to attach reinforced tissue patch 1000 to humerus "H".

In one embodiment, after the bone defect or defects have been created, the bone plug or plugs are secured within the bone defects by any suitable press-fitting technique. The bone to bone fit of a surface of the bone segment or segments within a surface, e.g., a wall, of the bone defect or defects creates an interference fit to minimize irritation at the operation site when the bone segment is inserted into the bone defect. Since the presently disclosed reinforce tissue patch 1000 may be made of autografts, allografts, and/or xenografts, the natural shape of the bone segment or segments may not match the contours of the humeral head "HH" of the humerus "H" and/or the bone defect. Therefore, accurate measurements and preparation, e.g., shaping of bone segment 1006 of patch 1000 and bone defect 1007 are taken in order to avoid potential complications (e.g., rubbing of surrounding tissues). This requires the length, width, and depth measurements of bone segment 1006 of patch 1000 to match the measurements of bone defect 1007 of the prepared humerus "H". Further, the contour of patch 1000 may also be matched to the contour of the humeral head "HH" of the humerus "H".

Reinforced tissue patch 1000 is attached to the rotator cuff tendon "T" by any attaching technique, for example, but not limited to, anchoring, suturing, adhering with a bioadhesive, screwing, plugging, press-fitting, clips, barbed sutures, and/or a combinations thereof. A useful and beneficial feature of the presently disclosed reinforced tissue patch 1000 is the ability to accurately measure the length of the patch needed to avoid over-tensioning of rotator cuff tendon "T" or any other native tendons, when patch 1000 is anatomically attached. As shown, reinforced tissue patch 1000 is attached to rotator cuff tendon "T" using sutures 1020.

In one method, one or more dehydrated (e.g., lyophilized) bone segments may be utilized in conjunction with a reinforced tissue patch according to the present disclosure. When the bone segments are dehydrated or lyophilized, this results in shrinkage of the bone segments. In this configuration, the dehydrated bone segments may then be positioned within the pre-drilled and/or shaped defects of humerus "H", whereupon rehydration of the bone segments will hydrate and expand to fill the defects, thus creating a tight, compressed fit between the bone plug and the defect.

In alternative embodiments, additional biologically active materials may be added to enhance healing of reinforced tissue patch 1000 to the humerus "H" and the tendon "T", which may include growth factors, demineralized bone matrix, cells, genes, peptides, drugs (including polymer drugs) growth factors (Bone Morphogenic Proteins such as BMP-2, 4, 7, 12, or 14; Platelet Derived Growth Factors e.g. PDGF-β; Insulin-Like Growth Factors, Fibroblast Growth Factors, or other appropriate growth factors), cells (autogenous, allogenic or xenogeneic fibroblasts, muscle, fat, mesenchymal stem cells, or other appropriate cells) or other agents which may facilitate the healing process. These biologically active materials, as well as those listed above, may be combined with any of the materials discussed herein including, but not limited to, tendons, grafts, sutures, adhesives, etc. Furthermore, these biologically active materials may be applied in situ as a solution or spray.

For a further discussion of the above disclosed method of repairing a rotator cuff, please refer to commonly owned U.S. Provisional Patent Application Ser. No. 61/153,676, filed Feb. 19, 2009, entitled "Method for Repairing a Rotator Cuff", the entire contents of which are incorporated herein by reference.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A reinforced tissue graft comprising:
   a tissue patch; and
   at least one barbed suture received within the tissue patch, wherein barbs of the at least one barbed suture are completely maintained within a thickness of the tissue patch, wherein the tissue patch is one of an allograft, a xenograft, or an autograft.

2. The reinforced tissue graft of claim 1, wherein the at least one barbed suture extends along a length of the tissue patch.

3. The reinforced tissue graft of claim 1, wherein the at least one barbed suture forms at least one of a Z-pattern or an X-pattern.

4. The reinforced tissue graft of claim 1, wherein the at least one barbed suture is in a spiral configuration.

5. The reinforced tissue graft of claim 1, wherein the at least one barbed suture is fixedly secured within the tissue patch.

6. The reinforced tissue graft of claim 1, wherein an entire length of the at least one barbed suture is completely maintained within the tissue patch.

7. The reinforced tissue graft of claim 1, wherein the at least one barbed suture includes a first barbed suture having a first diameter and a second barbed suture having a second diameter.

8. The reinforced tissue graft of claim 1, wherein the at least one barbed suture includes a first barbed suture having barbs extending in a first direction and a second barbed suture having barbs extending in a second direction.

* * * * *